United States Patent [19]

McGinnis

[11] Patent Number: 4,501,273
[45] Date of Patent: Feb. 26, 1985

[54] ENDOTRACHEAL TUBE WITH PRESSURE CONTROLLED INFLATABLE CUFF

[76] Inventor: Gerald E. McGinnis, 131 Kelvington Dr., Monroeville, Pa. 15146

[21] Appl. No.: 432,067

[22] Filed: Sep. 30, 1982

[51] Int. Cl.³ .................................................. A61M 25/00
[52] U.S. Cl. ..................................................... 128/207.15
[58] Field of Search ....................... 128/207.14, 207.15, 128/207.16, 207.18; 604/97, 98, 99, 100

[56] References Cited

U.S. PATENT DOCUMENTS

| | | | |
|---|---|---|---|
| 3,642,005 | 2/1972 | McGinnis | 128/351 |
| 3,794,043 | 2/1974 | McGinnis | 128/349 BV |
| 4,119,101 | 10/1978 | Igich | 128/207.15 |
| 4,159,722 | 7/1979 | Walker | 128/207.15 |

Primary Examiner—Henry J. Recla
Assistant Examiner—Karin M. Reichle
Attorney, Agent, or Firm—Carothers & Carothers

[57] ABSTRACT

One end of an endotracheal tube is encircled by an inflatable cuff, to which is connected a tubule that extends toward the opposite end of the tube and into a valve housing having an air inlet bore from which passages extend to the tubule and to an inflatable member. The bore contains valve means normally closing off the inlet of the bore, and means for opening the valve to admit air under pressure or to release it therefrom to inflate and deflate the cuff and inflatable member. A constant pressure means is disposed in the housing for exerting a substantially constant bias against the inflatable member throughout a predetermined range of expansion of the inflatable member to maintain preset air inflation pressures within the inflatable member and the cuff substantially constant, even though their respective inflation volumes may vary. An additional feature resides in the fact that the inflatable member is enclosed in the housing and the housing is sealed for expansion and contraction of the inflatable member within the sealed housing, and another tubule communicates the interior of this sealed housing with the interior of the endotracheal tube thereby preventing collapse of the inflated cuff when gas pressures within the endotracheal tube exceed the cuff inflation pressure.

4 Claims, 2 Drawing Figures

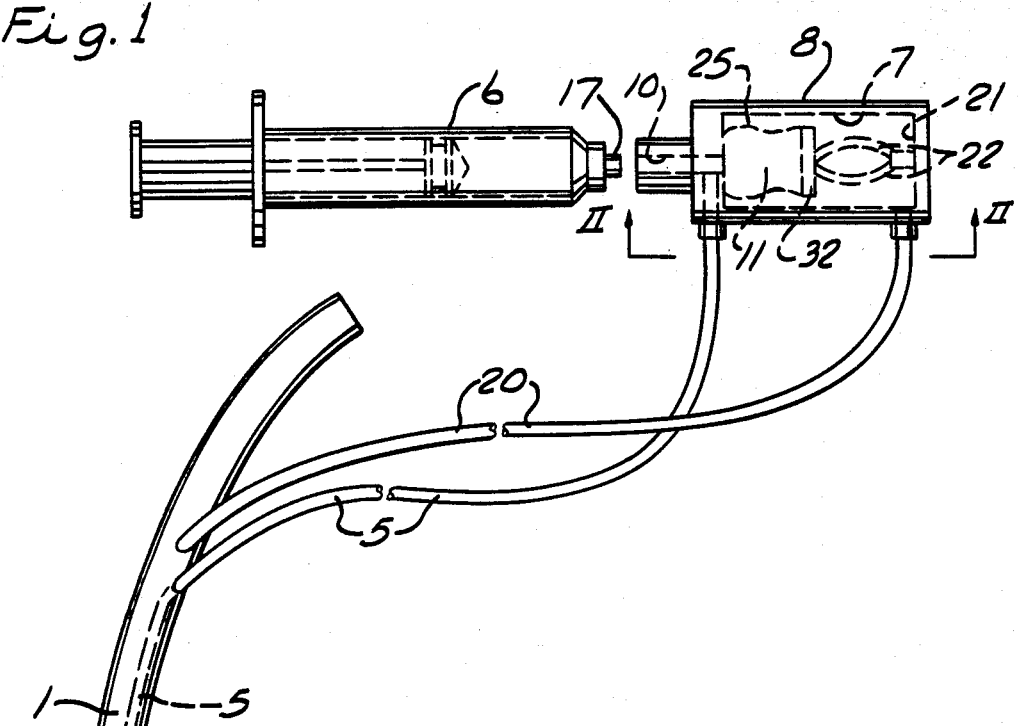
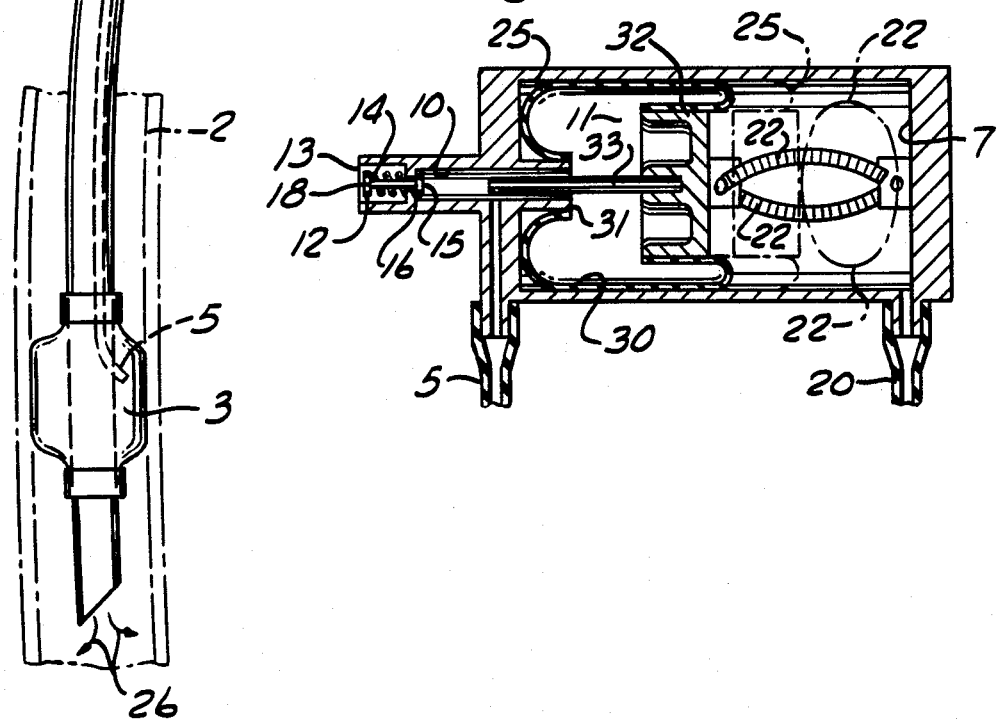

ENDOTRACHEAL TUBE WITH PRESSURE CONTROLLED INFLATABLE CUFF

The present invention relates to tubes for insertion into cavities of the body such as the trachea, bladder, or arteries, and which are retained in position in the body cavity, or which otherwise use an inflatable cuff. The present invention pertains in particular to controlling the inflation of the cuff in the body cavity, and the apparatus of the present invention may be provided as an integral part of the tube or as an adapter to an existing system.

While the teachings of the present invention are applicable to tubes for use in more than one type of body cavity, description will be made with respect to endotracheal tubes for convenience sake.

In my U.S. Pat. Nos. 3,642,005 and 3,794,043, an endotracheal tube with an inflatable cuff and a pressure regulating balloon is shown. Air is forced into the cuff, such as by a syringe detachably connected to the outer end of a tubule leading into the cuff, in order to expand the cuff against the wall of the trachea to prevent leakage between them when a respirator connected to the endotracheal tube forces air into the lungs. The outer end portion of the tubule opens into a balloon that is expanded along with the cuff. The balloon is of such a character that it will expand to a size at which the air pressure in it is the same as the maximum pressure desired in the cuff, after which the balloon will expand further without increasing the maximum pressure as additional air is forced into it. This prevents the cuff from becoming over-inflated and injuring the patient.

My latter-mentioned Patent improves on this combination by additionally providing a check valve which prevents the escape of air from the cuff into the inflatable member in case the outside of the cuff is subjected to sudden pressure. Occasionally it happens that the respirator connected to the endotracheal tube may deliver air to the patient at such a high pressure that it will compress the cuff by forcing air back into the balloon, thereby breaking the seal between the cuff and the trachea wall so that the air delivered by the respirator can escape past the cuff. In order to prevent this, my latter-mentioned invention provides a check valve system wherein the air from the balloon can always flow freely into the cuff, but in the reverse direction only at a very slow rate.

While the instrument shown in my latter-mentioned Patent does serve its purposes, it nevertheless does have drawbacks in that the check valve arrangement between the cuff and balloon cannot insure that the pressure within the inflated cuff will not be exceeded by the pressure of air or gases delivered to the patient through the interior of the endotracheal tube, such that the seal between the cuff and the trachea wall will be broken so that the air or gas delivered to the respirator can escape past the cuff. This is so because the check valve arrangement does permit, by necessity, air flow in the reverse direction at a very slow rate from the cuff to the balloon, and additionally because there is no means provided to automatically increase the pressure within the cuff in proportion to the increase of gas pressure delivered to the interior of the endotracheal tube.

It is accordingly a principal object of the present invention to provide an endotracheal tube with an inflatable cuff wherein the preset air pressure within the inflated cuff will be assured of remaining substantially constant, regardless of the respective inflation volume of the cuff and balloon or inflatable member.

It is another principal object of the present invention to provide an endotracheal tube with an inflatable cuff wherein the inflation pressure within the inflated cuff will automatically increase in proportion with the increases in pressure fed to the interior of the endotracheal tube, thereby preventing breakdown or leakage in the seal between the inflated cuff and the trachea wall.

The endotracheal tube with a controlled inflatable cuff of the present invention provides a constant pressure means which continually exerts a substantially constant bias against the inflatable member throughout a predetermined range of expansion of the inflatable member, thereby maintaining preset air inflation pressures within the inflatable member and the cuff substantially constant even though their respective inflation volumes may vary.

In a preferred embodiment, this constant pressure means consists of at least one constant force compression coil spring which extends between the inflatable member and the wall of a support housing for the inflatable member, such that the spring is bowed outwardly and thereby urges the inflatable member towards compression. The bowed spring is of a special design such that it exerts a substantially constant pressure against the inflatable member as it expands or contracts within a given range.

In the combination of the present invention, it is preferable that the inflatable member or balloon be constructed such that it is never stretched under contracting tension by inflation pressure, so that the stretch properties of the balloon or inflatable member materials do not influence the fluid pressure within the cuff and inflatable member. Rather, the inflation of the cuff at a prescribed pressure is determined by the physical property of the constant pressure means or springs bearing against the balloon assembly or inflatable member. Thus, the inflatable member expands and contracts within the desired working pressures involved without stretching, and therefore may be described as being non-extensible in this regard.

Another feature of the endotracheal cuff pressure control system of the present invention resides in a unique combination wherein the inflatable member is housed for expansion and contraction within a sealed housing. The interior of the sealed housing is then caused to communicate with the interior of the endotracheal tube either directly or through the ventilator tube or other means, by means of another or second tubule. Thus, as gas pressures increase within the airway, these gases are also introduced into the sealed housing, thereby exerting the same pressures against the inflatable member housed therein. This in turn proportionately increases the pressure within the inflatable member and the cuff with the pressure of the gases within the endotracheal tube interior, thereby preventing collapse of the cuff and leaking of the seal between the cuff and the trachea wall. This particular feature of the present invention is workable with an extensible or stretchable inflatable member, or with the non-extensible inflatable member hereinbefore described with my constant pressure means for maintaining constant pressures within the inflatable member.

Other objects and advantages appear in the following description and claims.

The accompanying drawings show, for the purpose of exemplification without limiting the invention or the claims thereto, certain practical embodiments illustrating the principles of this invention wherein:

FIG. 1 is a side view of the endotracheal tube with inflatable cuff of the present invention;

FIG. 2 is an enlarged view in vertical cross section, as seen along section line II—II, of the pressure regulator shown in the combination of FIG. 1.

Referring to the drawings, a flexible breathing tube 1, that is adapted to be inserted into a trachea 2, has an outer or proximal end for connection to a breathing apparatus such as a respirator (not shown) that will periodically force air into the lungs through the tube. The tube is encircled near its inner or distal end by a flexible cuff 3, that is attached to the tube and forms an air chamber around it. The cuff normally is more or less collapsed against the tube so that it and the tube can be inserted in the trachea. The surgeon selects a tube diameter based on his estimate of the diameter of the trachea. In order to inflate the cuff so as to form a seal with the wall of the trachea, a much smaller tube or tubule 5 is connected with the inside of the cuff and extends out along the inside of the larger tube 1 and then exists as illustrated in the Figure.

The proximal inlet of tubule 5 communicates with the interior of inflatable member 25, which in turn is expandable within chamber 7 of the sealed housing member 8. Sealed housing 8 is also provided with an air inlet bore 10 communicating with the tubule inlet of tubule 5 and with the interior 11 of inflatable member 25.

A push valve 12 (see FIG. 2) is provided within the inlet bore 10 and normally closes the inlet 13 thereof. Normally closed valve 12 consists of a simple valve structure normally biased to a closed position by compression spring 14 such that valve head 15 normally closes off and seats against annular valve seat 16.

When it is desired to insert air under pressure into inlet 13, the tip 17 of conventional syringe 6 is inserted to inlet 13 and thereby depresses contact head 18 of valve 12 inwardly against the compession bias of spring 14 to unseat valve head 15 from annular seat 16 and permit gases under pressure to flow through bore 10 from the plunger action of syringe 6 to inflate cuff 3 and inflatable member 25. In view of the fact that inflatable member 25 and cuff 3 have their interiors communicating with each other, they inflate with equal pressures. The result is, as inflatable member 25 is inflated via syringe 6 through check valve 12, so also inflatable cuff 3 inflates with the same interior pressure to seal off the inner wall of trachea 2.

Inflatable member 25 is also enclosed within the sealed chamber 7 of sealed housing 8 for expansion and contraction therein, and a second tubule 20 communicates the sealed interior 7 of housing 8 with the interior of endotracheal tube 1.

In order to maintain a constant pressure at a preset or predetermined value within inflatable member 25 and cuff 3, constant pressure means is provided or disposed in sealed housing 8 between inflatable member 25 and interior wall 21 of the sealed housing in the form of two constant force compression coil springs 22. Springs 22 are constantly bowed outwardly as indicated in their natural state, thereby urging inflatable member 25 into compression. These springs 22 exert a substantially constant pressure against inflatable member 25 as it expands from its contracted position as indicated in full lines in FIG. 2 to its expanded position as indicated by the chain outline. Springs 22 exert a substantially constant force against inflatable member 25 as it expands or contracts throughout a predetermined limited range as indicated to maintain preset air inflation pressures within the inflatable member 25 and cuff 3 substantially constant even though their respective inflation volumes may vary.

Springs 22 are constant force compression springs, in which the coil spring wire is provided with a large initial axial tension between the adjacent turns. As the spring is flexed to bow it, the turns separate along the convex side of the bow and are pressed more tightly together along the concave side of the bow. Such a spring is disclosed in U.S. Pat. No. Re 23,974, entitled Constant Compression Springs. These previously-patented springs are sold by The Hunter Spring Division of Ametek, Inc. under the trademark Flex'ator. When these springs are bowed, the resulting torque that tends to straighten them provides a substantially constant force throughout a convenient range of motion. Another use of this type of spring is illustrated in my U.S. Pat. No. 4,298,023 entitled Spring Loaded Exhalation Valve.

As previously noted, the interior 7 of sealed housing 8 communicates with the interior of endotracheal tube 1 via tubule 20. Thus, as gases under pressure are injected into the interior of tube 1 from the proximal end thereof, and pass through the tube and exit at the distal end thereof in the trachea 2 as indicated by the arrows 26, this gas pressure is also passed from the interior of tube 1 through the tubule 20 into the interior 7 of sealed housing 8, such that these gas pressures also act against inflatable member 25, tending to collapse it under pressure and thereby increase the gas pressure sealed within interior 11, and to correspondingly increase the gas pressure contained within inflated cuff 3. Thus, as the gas under pressure exits into the interior of trachea 2 as indicated at 26 and increases, the pressure within inflated cuff 3 will correspondingly or proportionately also increase to prevent collapsing of the cuff 3, thereby preventing leakage or breakdown of the seal between inflated cuff 3 and the internal wall of trachea 2. It is thus insured that cuff 3 does not over-inflate to cause injury, and on the other hand, it is also insured that inflated cuff 3 will always be inflated with sufficient air under pressure to prevent leakage automatically.

Inflatable member 25 consists of a sleeve-like flexible section of material 30 which is annularly sealed by gluing or other means to hub 31, and annularly sealed at its other end by similar means to the annular periphery of piston 32. Piston 32 is provided with a center piston guide rod 33 which is very loosely received within bore 10 to permit reasonable guided axial movement of piston 32 without restricting the passage of gases under pressure through inlet bore 10 into interior 11 of inflatable member 25 and into the inlet or interior of tubule 5.

Inflatable member 25 may be considered non-extensible in the sense that in its collapsed or fully inflated position as illustrated in FIG. 2, the flexible fabric 30 thereof is never placed in a stretched tension condition, as would be the case with a normally inflated balloon. Thus, there are no inflation contraction influences exerted on inflatable member 25 due to stretching capabilities thereof, and accordingly, all pressure regulation is controlled by the prescribed pressure determined by the physical properties of the springs 22.

It can thus be seen that the pressure within cuff 3 will always be assured to remain constant due to the forces applied against inflatable member 25 by constant pressure means 22. This constant pressure means is preferably provided in the form of the special springs 22 illustrated, however, it should be kept in mind that other constant pressure application means could be substituted, although less effectively, such as weights which are vertically supported on top of the inflatable member 25. Also, a pressure indicator may be conveniently provided for the pressure of inflation for inflatable member 25 and cuff 3 by making housing 8 of transparent materials so that the extent of expansion of inflatable member 25 may be observed therein. Suitable markings may be provided on the cylindrical surface of sealed housing 8 so that it will be known when the desired pressure within inflatable member 25 has been obtained, such that the top of piston 32 axially moves against the compression of springs 22 until it comes in line with the indicator (not shown) on housing 8.

Also, in view of the fact that inflatable member 25 is housed completely within chamber 6 of sealed housing 8, which in turn is in communication with the interior of tube 1, it becomes impossible for inflated cuff 3 to collapse sufficiently to leak because as gases increase in pressure at 26 within trachea 2, the internal pressures within cuff 3 must also correspondingly increase to counteract this, thereby preventing leakage between cuff 3 and trachea 2 and still further insuring that there is no injury to the patient. As soon as the gas pressures at 26 decrease, the pressures within cuff 3 also correspondingly and automatically decrease.

I claim:

1. In combination, an endotracheal tube having distal and proximal ends, a normally collapsed flexible tubular cuff encircling the tube near its distal end and having opposite ends sealed thereto, a tubule extending from the cuff outwardly along said tube and having a distal end communicating with the inside of the cuff, the proximal end of the tubule having an inlet for air under pressure for inflating the cuff, an inflatable member, the tubule inlet fluidically communicating with the interior of the inflatable member, a valve housing provided with an air inlet bore fluidically communicating with the tubule inlet and interior of the inflatable member, valve means in the bore normally closing the inlet thereof, means for opening the valve means to admit air under pressure through said inlet bore to inflate the cuff and the inflatable member, the improvement comprising, said inflatable member mounted within said valve housing for expansion and contraction therein and including constant pressure means disposed in said valve housing between said inflatable member and said valve housing for exerting a substantially constant bias against said inflatable member throughout a predetermined range of expansion of said inflatable member in said valve housing whereby air inflation pressures within said inflatable member and said cuff are maintained substantially constant even though their respective inflation volumes may vary.

2. The combination recited in claim 1, said constant pressure means including at least one constant force compression coil spring extending between said inflatable member and an interior wall of said valve housing, and means on said interior wall and said inflatable member for connecting respective ends of the spring thereto, said spring being bowed outwardly and thereby urging said inflatable member toward compression, said spring exerting a substantially constant pressure against said inflatable member as it expands or contracts.

3. The combination recited in claim 1 or 2, wherein said valve housing is a sealed housing, and includes a second tubule fluidically communicating the interior of said sealed housing exterior of said inflatable member with the interior of said endotracheal tube.

4. The combination recited in claim 1 or 2, wherein said inflatable member is non-extensible whereby it is not subjected to contraction stretch forces due to properties of its construction material under inflation.

* * * * *